United States Patent [19]

Monnais et al.

[11] Patent Number: 4,863,481
[45] Date of Patent: Sep. 5, 1989

[54] DYEING COMPOSITIONS BASED ON OXIDATION DYESTUFF PRECURSORS AND ON N-SUBSTITUTED ORTHO-NITROANILINES AND COMPRISING AN ALKANOLAMINE AND BISULPHITE, AND THEIR USE IN THE DYEING OF KERATIN FIBRES

[75] Inventors: Christian Monnais, Neuilly-sur-Seine; Jean Cotteret, Franconville, both of France

[73] Assignee: L'Oreal, Paris, France

[21] Appl. No.: 455,039

[22] Filed: Jan. 3, 1983

[30] Foreign Application Priority Data

Jan. 5, 1982 [FR] France .................... 82 00066

[51] Int. Cl.$^4$ ................................ A61K 7/13
[52] U.S. Cl. ........................... 8/414; 8/405; 8/406; 8/407; 8/408; 8/415; 8/428
[58] Field of Search .................. 8/405, 406, 407, 408, 8/414, 415, 428

[56] References Cited

U.S. PATENT DOCUMENTS

| | | | |
|---|---|---|---|
| 3,555,584 | 1/1971 | Kalopissis et al. | 8/407 |
| 3,698,852 | 10/1972 | Pantzer et al. | 8/408 |
| 3,733,175 | 5/1973 | Alperin et al. | 8/407 |
| 3,951,589 | 4/1976 | Alperin et al. | 8/907 |
| 3,973,900 | 8/1976 | Husemeyer et al. | 8/407 |
| 4,337,061 | 6/1982 | Bugaut et al. | 8/405 |
| 4,417,896 | 11/1983 | Bugaut et al. | 8/407 |
| 4,419,101 | 12/1983 | Bugaut et al. | 8/407 |
| 4,432,769 | 2/1984 | Bugaut et al. | 8/407 |

FOREIGN PATENT DOCUMENTS

| | | |
|---|---|---|
| 1061515 | 3/1967 | United Kingdom . |
| 1104970 | 3/1968 | United Kingdom . |
| 1164824 | 9/1969 | United Kingdom . |
| 1403928 | 8/1975 | United Kingdom . |
| 1447788 | 9/1976 | United Kingdom . |
| 2003938 | 9/1978 | United Kingdom . |
| 2078747 | 1/1982 | United Kingdom . |
| 2085484 | 4/1982 | United Kingdom . |

OTHER PUBLICATIONS

Sidi et al., Problems Of Hair Care, Clinical, Biological And Physiochemical Study Of Female Hair.
McGraw-Hill Dictionary Of Scientific And Technical Terms (D. N. Lapedes ed.), McGraw-Hill, Inc. (1978), pp. 537, 1027.
Webster's New Univsersal Unabridged Dictionary (J. L. McKechnie ed.), Simon & Schuster (1983), pp. 596, 1141.
Sidi et al., Problemes Capillaires, pp. 118–119, 143.

*Primary Examiner*—Douglas W. Robinson
*Attorney, Agent, or Firm*—Fleit, Jacobson, Cohn, Price, Holman & Stern

[57] ABSTRACT

The invention relates to oxidation dyeing compositions comprising oxidation dyestuff precursors and N-substituted ortho-nitroanilines of the formula:

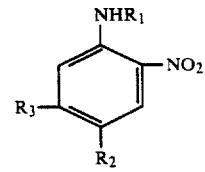

in which $R_1$ denotes an alkyl, monohydroxyalkyl or polyhydroxyalkyl group, $R_2$ denotes hydrogen or an amino, monoalkylamino, dialkylamino, mono- or di-(monohydroxyalkyl or polyhydroxyalkyl)-amino, (N-alkyl-N-monohydroxyalkyl or N-alkyl-N-polyhydroxyalkyl)-amino, alkoxy, monohydroxyalkoxy, polyhydroxyalkoxy or aminoalkoxy group and $R_3$ denotes hydrogen or an alkyl group, at least one of $R_2$ and $R_3$ being different from H, with the proviso that if $R_1$ denotes $-CH_2CH_2OH$, $R_2$ cannot be di-(monohydroxyalkyl)-amino in an alkaline medium which is non-ammoniacal and comprises an alkali metal or ammonium bisulphite and at least one alkanolamine which is N-($C_1$ to $C_4$-alkyl-ethanolamine, N,N-di($C_1$ to $C_4$-alkyl)-ethanolamine, di-(hydroxy-$C_2$ to $C_3$-alkyl)-amine, 2-amino-2-methylpropan-1-ol, 2-dimethylamino-2-methylpropan-1-ol, 2-amino-2-ethylpropane-1,3-diol, 2-amino-2-methylpropane-1,3-diol or 2-amino-2-hydroxymethylpropane-1,3-diol.

16 Claims, No Drawings

DYEING COMPOSITIONS BASED ON OXIDATION DYESTUFF PRECURSORS AND ON N-SUBSTITUTED ORTHO-NITROANILINES AND COMPRISING AN ALKANOLAMINE AND BISULPHITE, AND THEIR USE IN THE DYEING OF KERATIN FIBRES

The present invention relates to dyeing compositions which are useful in oxidation dyeing and which comprise oxidation dyestuff precursors in association with N-substituted ortho-nitroanilines, it being possible for these compositions to be used for dyeing keratin fibres, and in particular human hair.

The use of oxidation dyestuff precursors is widespread in the field of hair dyeing. This class of dyestuffs comprises compounds which are initially only slightly coloured or colourless; they are commonly called "oxidation bases" and develop their tinctorial strength within the hair in the presence of one or more oxidising agents, leading to the formation of coloured compounds. The formation of these coloured compounds results either from oxidative condensation of the "oxidation bases" with themselves, or from oxidative condensation of the "oxidation bases" with compounds commonly called "couplers", which are generally present in the dyeing compositions used in oxidation dyeing.

The variety of molecules used, namely, on the one hand, the "oxidation bases" and, on the other hand, the "couplers", makes it possible to obtain a very wide range of natural or ashen tints, which cannot easily be obtained by other means.

In general, these tints also possess excellent properties for hiding white hair. Furthermore, they are generally fairly fast to external agents such as light and washing.

On the other hand, in terms of the sheen of the colours, if it is desired to obtain warm shades such as golden, coppery, mahogany or red shades, satisfactory "oxidation base"-"coupler" combinations are rare. They frequently have a low fastness to light, which, in certain cases, causes the shade on the hair to change with time, with a loss of sheen. Furthermore, in this type of shade, combinations of oxidation dyestuff precursors are frequently found to be inadequate due to their lack of luminosity.

To overcome these two disadvantages, it is well known to use direct dyestuffs, that is to say coloured substances providing a colouration in the absence of an oxidising agent, in association with oxidation dyestuff precursors. Their use in oxidation dyeing obviously requires stability in the oxidising medium which enables the oxidation dyestuff precursors to develop their colour during the application of the dye.

Nitro direct dyestuffs generally satisfy this condition.

However, the direct dyestuffs used in oxidation dyeing must fulfil an additional condition, namely that of being stable in an alkaline reducing medium.

In fact, compositions comprising oxidation dyestuff precursors generally comprise an alkaline compound, the purpose of which is to decompose the oxidising agent, the latter thus making it possible to ensure the desired lightening and oxidation, and also a reducing compound to prevent premature oxidation of the oxidation dyestuff precursors during manufacture and storage of the dyeing composition.

One of the most widely used alkaline reducing systems is ammonia+sodium bisulphite. Now, a very large number of nitro dyestuffs are unstable in a conventional alkaline reducing medium of this type; this is the case, in particular, of the orange, red and purplish-blue dyestuffs of the formula:

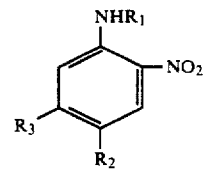

in which $R_1$ denotes an alkyl, monohydroxyalkyl or polyhydroxyalkyl group, $R_2$ denotes hydrogen or an amino, monoalkylamino, dialkylamino, mono- or di-(monohydroxyalkyl or polyhydroxylalkyl)-amino, (N-alkyl-N-monohydroxyalkyl or N-alkyl-N-polyhydroxyalkyl)-amino, alkoxy, monohydroxyalkoxy, polyhydroxyalkoxy or aminoalkoxy group and $R_3$ denotes hydrogen or an alkyl group, at least one of the substituents $R_2$ or $R_3$ being different from hydrogen, with the proviso that if $R_1$ denotes the group $-CH_2CH_2OH$, $R_2$ cannot be a di-(monohydroxyalkyl)-amino group.

In fact, in the medium comprising ammonia+sodium bisulphite, a very rapid change in the dyestuffs of type (I) takes place and they are converted to dyestuffs of type (II):

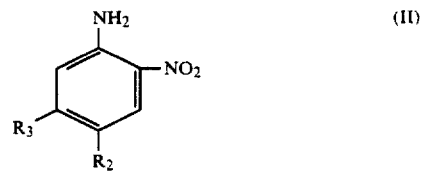

in which $R_2$ and $R_3$ have the same meaning as for the dyestuffs of type (I).

It seems that this change is capable of taking place in the absence of a reducing agent, but much more slowly. In this case, the sodium bisulphite acts as an acceleration of the conversion reaction.

We have discovered that, surprisingly, the use of a well-defined family of alkanolamines makes it possible to prevent, or very greatly to retard, the abovementioned conversion, even in the presence of the powerful activator which sodium bisulphite or another alkali metal bisulphite represents.

The present invention therefore provides a dyeing composition for the oxidation dyeing of keratin fibres, and in particular human hair, in an alkaline reducing medium, comprising at least one oxidation dyestuff precursor and at least one N-substituted ortho-nitroaniline in an aqueous vehicle, characterised in that the N-substituted ortho-nitroaniline or ortho-nitroanilines are chosen from amongst the compounds of the formula:

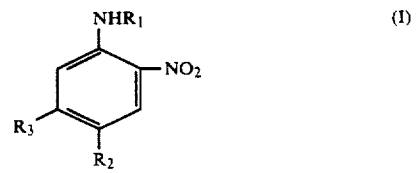

in which $R_1$, $R_2$ and $R_3$ are as defined above, and their cosmetically acceptable salts, and in that the alkaline reducing medium used is non-ammoniacal and comprises an alkali metal or ammonium bisulphite and at least one alkanolamine chosen from amongst: N-(C$_1$-C$_4$-alkyl)-ethanolamines, N,N-di-(C$_1$-C$_4$-alkyl)-ethanolamines, di-(hydroxy-C$_1$-C$_3$-alkyl)-amines, 2-amino-2-methylpropan-1-ol, 2-dimethylamino-2-methylpropan-1-ol, 2-amino-2-ethylpropane-1,3-diol, 2-amino-2-methylpropane-1,3-diol and 2-amino-2-hydroxymethylpropane-1,3-diol.

The term "alkyl group" in the compounds of formula (I) as used herein means a C$_1$-C$_6$-alkyl group and more particularly a methyl, ethyl, n-propyl, isopropyl, n-butyl, isobutyl or tert.-butyl group. Likewise, the term "alkoxy group" means a C$_1$-C$_6$-alkoxy group and more particularly a methoxy, ethoxy, n-propoxy, isopropoxy, n-butoxy, isobutoxy or tert.-butoxy group.

The present invention also provides a process for dyeing keratin fibres, and in particular human hair, using a dyeing composition of the present invention.

The bisulphite used as the reducing agent in the dyeing composition according to the invention is typically a sodium, potassium or ammonium bisulphite.

The N-(C$_1$-C$_4$-alkyl)-ethanolamines preferably used in the invention are: N-methylethanolamine, N-ethylethanolamine, N-propylethanolamine, N-isopropylethanolamine, N-butylethanolamine and N-tert.-butylethanolamine.

The preferred N,N-di-(C$_1$-C$_4$-alkyl)-ethanolamines are: N,N-dimethylethanolamine, N,N-diethylethanolamine, N-methyl-N-ethylethanolamine and N-methyl-N-propylethanolamine.

Preferred di-(hydroxy-C$_2$-C$_3$-alkyl)-amines which may be mentioned are: diethanolamine and diisopropanolamine.

The N-substituted ortho-nitroanilines of the formula (I) which are advantageously used in the present invention are as follows:

2-N-methylamino-5-aminonitrobenzene, 2-N-($\beta$-hydroxyethyl)-amino-5-aminonitrobenzene, 2-N-($\beta$-hydroxyethyl)-amino-5-N-($\beta$-hydroxyethyl)-aminonitrobenzene, 2-N-($\beta$-hydroxyethyl)-amino-5-(N-methyl-N-$\beta$-hydroxyethyl)-aminonitrobenzene, 2-N-($\beta$-hydroxyethyl)-amino-5-N-methylaminonitrobenzene, 2-N-methylamino-5-N-methylaminonitrobenzene, 2-N-methylamino-5-(N-methyl-N-$\beta$-hydroxyethyl)-aminonitrobenzene, 2-N-methylamino-5-(N-methyl-N-$\beta,\gamma$-dihydroxypropyl)-aminonitrobenzene, 2-N-methylamino-5-N,N-bis-($\beta$-hydroxyethyl)-aminonitrobenzene, 2-N-methylamino-5-methoxynitrobenzene, 2-N-($\beta$-hydroxyethyl)-amino-5-methoxynitrobenzene, 2-N-($\beta$-hydroxyethyl)-amino-4-methyl-5-aminonitrobenzene, 2-N-($\gamma$-hydroxypropyl)-amino-5-N-($\beta$-hydroxyethyl)-aminonitrobenzene, 2-N-methylamino-5-($\beta$-hydroxyethoxy)-nitrobenzene, 2-N-($\beta$-hydroxypropyl)-amino-5-N-($\beta$-hydroxyethyl)-aminonitrobenzene, 2-N-($\beta,\gamma$-dihydroxypropyl)-amino-5-N-($\beta$-hydroxyethyl)-aminonitrobenzene, 2-N-methylamino-5-N-($\beta$-hydroxyethyl)-aminonitrobenzene, 2-N-($\beta$-hydroxyethyl)-amino-5-($\beta$-methoxyethoxy)-nitrobenzene, 2-N-($\beta$-hydroxyethyl)-amino-5-($\beta$-hydroxyethoxy)-nitrobenzene, 2-N-($\beta$-hydroxyethyl)-amino-5-($\beta,\gamma$-dihydroxypropoxy)-nitrobenzene and 2-N-($\beta$-hydroxyethyl)-amino-5-($\beta$-hydroxypropoxy)-nitrobenzene.

These compounds can be used in the form of their cosmetically acceptable salts.

The dyeing composition according to the invention typically comprises 0.01 to 3% by weight of at least one dyestuff of the formula (I), 0.001 to 10% by weight of at least one oxidation dyestuff precursor, 0.1 to 30% by weight of at least one alkanolamine as defined above, and 0.1 to 4% by weight of the bisulphite.

Preferably, the composition according to the invention comprises 0.05 to 2% by weight of at least one dyestuff of the formula (I), 0.01 to 5% by weight of at least one oxidation dyestuff precursor, 1 to 25% by weight of at least one alkanolamine as defined above, and 0.2 to 2% by weight of bisulphite.

By virtue of the presence, in the dyeing composition of the invention, of an alkanolamine of the class defined above, the dyestuff of the formula (I) keeps very well during storage before use, and therefore retains its tinctorial strength.

The oxidation dyestuff precursors used in the dyeing composition according to the invention may belong to the following classes: para-phenylenediamines, para-aminophenols, para-diphenols, ortho-aminophenols, ortho-phenylenediamines, and heterocyclic bases such as pyridine bases or pyrimidine bases. These compounds can optionally be substituted on the amine groups and on the benzene or heterocyclic rings.

The dyeing compositions according to the invention can also comprise one or more toners or couplers. Couplers which can be used include phenols, meta-diphenols, meta-aminophenols and meta-phenylenediamines. These compounds can optionally be substituted on the amine groups, on the phenolic hydroxyl groups and on the benzene ring.

Other couplers which can be used include monohydroxy or dihydroxy derivatives of naphthalene, and also heterocyclic compounds, pyrazolones or diketone compounds. These derivatives can be substituted on the non-monovalent radicals and also on the aromatic and heterocyclic rings.

It is of course possible to introduce other direct dyestuffs into the dyeing compositions according to the invention, and, in particular, nitro derivatives of the benzene series having a different structure from that of the dyestuffs of the formula (I), which are already stable in the presence of ammonia and bisulphite.

The dyeing compositions according to the invention can contain anionic, cationic, non-ionic or amphoteric surface-active agents or mixtures thereof. Amongst the preferred surface-active agents, there may be mentioned, more particularly, soaps, alkylbenzenesulphonates, alkylnaphthalenesulphonates, quaternary ammonium salts, fatty acid diethanolamides and polyoxyethyleneated or polyglycerolated acids, alcohols or amides.

The surface-active agents are typically present in the compositions according to the invention in an amount from 0.1 to 55% by weight and preferably from 1 to 40% by weight, relative to the total weight of the composition.

The dyeing compositions according to the invention can also contain organic solvents: examples of these which may be mentioned include lower alkanols such as ethanol or isopropanol, glycerol, glycols or glycol ethers, such as ethylene glycol monobutyl ether, ethylene glycol, propylene glycol, and diethylene glycol monoethyl ether and monomethyl ether, and analogous products or mixtures thereof.

These solvents are preferably used in an amount from 1 to 50% by weight, and more particularly from 3 to 30% by weight, relative to the total weight of the composition.

The dyeing compositions according to the invention can also contain anionic, non-ionic, cationic or amphoteric polymers, generally in an amount from 0.1 to 5% by weight.

The dyeing compositions according to the invention can be thickened, preferably with sodium alginate, gum arabic, cellulose derivatives such as methylcellulose, hydroxyethylcellulose, hydroxypropylmethylcellulose and carboxymethylcellulose, or various polymers which serve this purpose, such as polymers of acrylic acid derivatives. It is also possible to use inorganic thickeners such as bentonite.

These thickeners are preferably present in an amount from 0.1 to 5% by weight and in particular from 0.5 to 3% by weight, relative to the total weight of the composition.

Of course, any other adjuvants normally used in hair-dyeing compositions, such as penetrating agents, sequestering agents, buffers and perfumes, can be included in the compositions according to the invention.

These ingredients can contribute towards giving the compositions according to the invention the desired cosmetic form, namely a more or less thickened liquid, a gel or a cream.

The pH of the dyeing compositions according to the invention is generally from 8 to 11.5.

At the time of use, the compositions according to the invention are mixed with an oxidising agent, which develops the colouration. This oxidising agent can be urea peroxide or a per-salt, but is most frequently hydrogen peroxide.

The dye is then applied to the hair for, say, 2 minutes to 1 hour, but preferably from 5 to 30 minutes. The hair is then rinsed, optionally shampooed and rinsed again, and dried.

The Examples which follow further illustrate the present invention.

EXAMPLE 1

2-Isopropyl-1,4-diaminobenzene dihydrochloride: 3.5 g

1-Amino-4-hydroxybenzene: 0.5 g 6-($\beta$-Hydroxyethoxy)-1,3-diaminobenzene dihydrochloride: 0.05 g 2-Methyl-1,3-dihydroxybenzene: 1 g 1-Hydroxy-3-aminobenzene: 1 g 1,4-Dihydroxybenzene: 0.1 g 2-N-($\beta$-Hydroxyethyl)-amino-5-($\beta$-hydroxyethoxy)-nitrobenzene: 0.4 g Oleyl alcohol glycerolated with 2 mols of glycerol: 5 g Oleyl alcohol glycerolated with 4 mols of glycerol: 5 g Oleic acid: 5 g Oleyldiethanolamine: 5 g Oleic diethanolamide: 12 g Ethanol: 10 g Ethylglycol: 12 g Ethylenediaminetetraacetic acid: 0.2 g 35° Bé strength sodium bisulphite solution: 1.3 g N-methylethanolamine: 8 g Distilled water, q.s.: 100 g This liquid composition is diluted at the time of use with an equal weight of an oxidizing milk of 20 volumes strength in respect to hydrogen peroxide. The gel obtained is applied to chestnut hair for 30 minutes. After rinsing, the hair is washed and then dried. It is then coloured a mahogany golden light chestnut shade.

If the N-methylethanolamine were replaced by ammonia, a change in the nitro dyestuff would be observed on storage, and this would result, in terms of the dyeing, in a distinctly yellower shade.

EXAMPLE 2

N,N-Bis-($\beta$-hydroxyethyl)-amino-4-aminobenzene sulphate: 0.3 g 1,4-Diaminobenzene: 0.3 g 1-Amino-4-hydroxybenzene: 0.5 g 1,3-Dihydroxybenzene: 1.2 g 1,4-Dihydroxybenzene: 0.15 g 2-N-($\beta$-Hydroxyethyl)-amino-5-methoxynitrobenzene: 0.4 g 2-N-($\beta$-Hydroxyethyl)-amino-5-N-methylaminonitrobenzene: 0.25 g Oleyl alcohol glycerolated with 2 mols of glycerol: 5 g Oleyl alcohol glycerolated with 4 mols of glycerol: 5 g Oleic acid: 5 g Oleyldiethanolamine: 5 g Oleic diethanolamide: 12 g Ethanol: 10 g Ethylglycol: 12 g Ethylenediaminetetraacetic acid: 0.2 g 35° Bé strength sodium bisulphite solution: 1.3 g N-Propylethanolamine: 5 g N,N-Dimethylethanolamine: 3 g Distilled water, q.s.: 100 g This composition is diluted at the time of use with an equal weight of an oxidizing milk of 20 volumes strength in respect to hydrogen peroxide. This gives a gel, which is applied to deep blond hair for 30 minutes. After rinsing, the hair is washed and dried. It is then coloured a golden blond shade. The nitro dyestuffs in this composition keep much better than in a similar composition in which the two alkanolamines have been replaced by ammonia.

EXAMPLE 3

2,3-Dimethyl-1,4-diaminobenzene dihydrochloride: 1 g

2-Methyl-1,3-dihydroxybenzene: 0.8 g 6-($\beta$-Hydroxyethoxy)-1,3-diaminobenzene dihydrochloride: 0.03 g 1,3-Dihydroxybenzene: 0.2 g 1-Hydroxy-3-aminobenzene: 0.2 g 1,4-Dihydroxybenzene: 0.1 g 2-N-($\beta$-Hydroxyethyl)-amino-5-N-($\beta$-hydroxypropoxy)-nitrobenzene: 0.3 g 2-Amino-4-methyl-5-N-($\beta$-hydroxyethyl)-aminonitrobenzene: 0.25 g Oleyl alcohol glycerolated with 2 mols of glycerol: 5 g Oleyl alcohol glycerolated with 4 mols of glycerol: 5 g Oleic acid: 5 g Oleyldiethanolamine: 5 g Oleic diethanolamide: 12 g Ethylglcyol: 12 g Ethanol: 10 g Etjhylenediaminetetraacetic acid: 0.2 g 35° Bé strength sodium bisulphite solution: 1.3 g N-Methylethanolamine: 8 g Distilled water, q.s.: 100 g This liquid composition is diluted with its own weight of an oxidizing milk of 20 volumes strength in respect to hydrogen peroxide. The gel obtained is applied to deep blond hair for 30 minutes. The hair is rinsed and then washed. After drying, it is coloured a red iridescent light blond shade.

If this composition contained ammonia in place of the N-methylethanolamine, the 2-N-(β-hydroxyethyl)-amino-5-(β-hydroxypropoxy)-nitrobenzene dyestuff would change to produce 2-amino-5-(β-hydroxypropoxy)-nitrobenzene on storage, which would lead to a yellower shade.

EXAMPLE 4

1,4-Diaminobenzene: 0.5 g
1-Amino-4-hydroxybenzene: 0.3 g
2-Methyl-1,3-dihydroxybenzene: 0.6 g
1-Hydroxynaphthalene: 0.05 g
1-Hydroxy-3-N,N-diethylaminobenzene: 0.1 g
2-N-Methylamino-5-N-(β-hydroxyethyl)-aminonitrobenzene: 0.3 g
2-N-Methylamino-5-(β-hydroxyethoxy)-nitrobenzene: 0.1 g
50/50 Mixture of cetyl and stearyl alcohols: 18 g
2-Octyldodecanol: 3 g
Cetyl/stearyl alcohol containing 15 mols of ethylene oxide: 3 g
Ammonium lauryl-sulphate containing 30% of active ingredient: 12 g
Polymer consisting of repeat units of the formula:

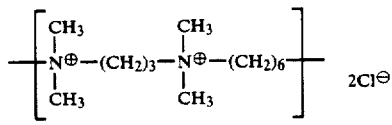

which can be prepared as described in French Patents 2,270,846 and 2,233,012: 3 g
35° Bé strength sodium bisulphite solution: 2 g
N-Propylethanolamine: 6.5 g
Distilled water, q.s.: 100 g This cream is diluted with 1.5 times its weight of an oxidizing milk of 20 volumes strength in respect to hydrogen peroxide. The cream obtained is applied to chestnut hair for 30 minutes. The hair is rinsed, washed and dried. The hair is coloured a coppery mahogany light chestnut shade.

In a similar composition in which the N-propylethanolamine had been replaced by ammonia, a rapid conversion of the nitro dyestuffs would be observed on storage, which would lead to a modification of the sheen obtained in the dyeing.

EXAMPLE 5

1,4-Diaminobenzene: 0.35 g
2-Chloro-1,4-diaminobenzene: 0.10 g
1-Amino-4-hydroxybenzene: 0.10 g
1,3-Dihydroxybenzene: 0.20 g
1-Hydroxy-3-aminonitrobenzene: 0.3 g
2-Methyl-1,3-dihydroxybenzene: 0.2 g
2-N-(β-Hydroxyethyl)-amino-5-(β-hydroxypropoxy)-nitrobenzene: 0.6 g
2-N-Methylamino-5-N,N-bis-(β-hydroxyethyl)-aminonitrobenzene: 0.4 g
Oleyl alcohol glycerolated with 2 mols of glycerol: 5 g
Oleyl alcohol glycerolated with 4 mols of glycerol: 5 g
Oleic acid: 5 g
Oleyldiethanolamine: 5 g
Oleic diethanolamide: 12 g
Ethanol: 10 g
Ethylglycol: 12 g
Ethylenediaminetetraacetic acid: 0.2 g
35° Bé strength sodium bisulphite: 1.3 g
N-Methylethanolamine: 7.5 g
Distilled water, q.s.: 100 g This liquid is diluted at the time of use with an equal weight of an oxidizing milk of 20 volumes strength in respect to hydrogen peroxide. This gives a gel, which is applied to chestnut hair for 30 minutes. The hair is rinsed, washed and dried after dyeing. It is then dyed an iridescent deep blond shade.

This composition makes it possible to obtain a storage stability of the nitro dyestuffs which is superior to that which would be obtained using ammonia as the alkaline lightening agent.

EXAMPLE 6

2,6-Dimethyl-1,4-diaminobenzene dihydrochloride: 0.7 g
6-(β-Aminoethoxy)-1,3-diaminobenzene dihydrochloride: 0.05 g
6-Methyl-1-hydroxy-3-N-(β-hydroxyethyl)-aminobenzene: 0.05 g
1,4-Dihydroxybenzene: 0.1 g
1,3-Dihydroxybenzene: 0.6 g
1-Phenyl-3-methylpyrazol-5-one: 0.15 g
1-Hydroxy-3-aminobenzene: 0.3 g
2-N-(β-Hydroxyethyl)-amino-5-(β,γ-dihydroxypropoxy)-nitrobenzene: 0.4 g
2-N-(β-Hydroxypropyl)-amino-5-N-(β-hydroxyethyl)-aminonitrobenzene: 0.2 g
2-N-Methylamino-5-(N-methyl-N-β-hydroxyethyl)-aminonitrobenzene: 0.2 g
Oleyl alcohol glycerolated with 2 mols of glycerol: 5 g
Oleyl alcohol glycerolated with 4 mols of glycerol: 5 g
Oleic acid: 5 g
Oleyldiethanolamine: 5 g
Oleic diethanolamide: 12 g
Ethanol: 10 g
Ethylglycol: 12 g
Ethylenediaminetetraacetic acid: 0.2 g
35° Bé strength sodium bisulphite solution: 1.3 g
N-Tert.-butylethanolamine: 7 g
Distilled water, q.s.: 100 g This liquid composition is mixed with an equal weight of an oxidizing milk of 20 volumes strength in respect to hydrogen peroxide. The gel obtained is applied to light chestnut hair. After a peirod of 30 minutes, the hair is rinsed, washed and dried. It is then dyed an iridescent ashen deep blond shade.

If the N-tert.-butylethanolamine is replaced by ammonia, a rapid change in the nitro dyestuffs is observed on storage, which leads to a modification of the sheen obtained on dyeing with the corresponding composition after storage, compared with a fresh composition.

EXAMPLE 7

1-N-(β-Methoxyethyl)-amino-4-aminobenzene dihydrochloride: 1.3 g
1,3-Dihydroxybenzene: 0.6 g
1-Hydroxy-3-aminobenzene: 0.65 g 6-(β-Hydroxyethoxy)-1,3-diaminobenzene dihydrochloride: 0.03 g
2-N-(β-Hydroxyethyl)-amino-5-N-(β-hydroxyethyl)-aminonitrobenzene: 0.3 g
2-N-(β-Hydroxyethyl)-amino-5-(β-hydroxypropoxy)-nitrobenzene: 0.25 g
2-Amino-3-hydroxynitrobenzene: 0.3 g
50/50 Mixture of cetyl and stearyl alcohols: 18 g
2-Octyldodecanol: 3 g
Cetyl/stearyl alcohol containing 15 mols of ethylene oxide: 3 g
Ammonium lauryl-sulphate containing 30% of active ingredient: 12 g
Polymer consisting of repeat units of the formula:

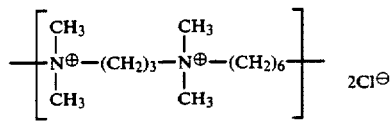

which can be prepared as described in
French Patents 2,270,846 and 2,233,012: 3 g
35° Bé strength sodium bisulphite solution: 2 g
N-Methylethanolamine: 6 g
Distilled water, q.s.: 100 g This composition is a cream, which is diluted with 1.5 times its weight of an oxidizing milk of 20 volumes strength in respect to hydrogen peroxide. The mixture obtained, which is of creamy consistency, is applied to deep chestnut hair for 30 minutes. After rinsing, shampooing and drying, the hair is coloured an iridescent light chestnut shade.

If the composition contained ammonia in place of the N-methylethanolamine, a rapid change of the two orthonitroanilines substituted on the amine group into unsubstituted structures would be observed, and this change would result in a rapid modification of the sheen of the shade obtained after storage of the composition.

EXAMPLE 8

2,6-Dimethyl-1,4-diaminobenzene dihydrochloride: 0.8 g
1-Amino-4-hydroxybenzene: 0.4 g
1,3-Dihydroxybenzene: 0.5 g
6-(β-Hydroxyethoxy)-1,3-diaminobenzene dihydrochloride: 0.05 g
1-Hydroxy-3-aminobenzene: 0.6 g
1,4-Dihydroxybenzene: 0.15 g
2-N-(β-Hydroxyethyl)-amino-5-aminonitrobenzene: 0.25 g
2-N-(β-Hydroxyethyl)-amino-5-N-(β-hydroxyethyl)-aminonitrobwnzene: 0.25 g
Oleyl alcohol glycerolated with 2 mols of glycerol: 5 g
Oleyl alcohol glycerolated with 4 mols of glycerol: 5 g
Oleic acid: 5 g
Oleyldiethanolamine: 5 g
Oleic diethanolamide: 12 g
Ethanol: 10 g
Ethylglycol: 12 g
Ethylenediaminetetraacetic acid: 0.2 g
35° Bé strength sodium bisulphite solution: 1.3 g
2-Amino-2-methylpropan-1-ol: 7 g
Distilled water, q.s.: 100 g This composition is in the form of a liquid, which is diluted at the time of use with an equal weight of an oxidizing milk of 20 volumes strength in respect to hydrogen peroxide. The gel obtained is applied to deep blond hair for 30 minutes. After rinsing, the hair is washed and dried. It is then coloured an iridescent blond shade.

If this composition were prepared with the 2-amino-2-methylpropanol being replaced by ammonia, the nitro dyestuffs contained in the composition would be rapidly degraded during storage.

EXAMPLE 9

1-N-(β-Methoxyethyl)-amino-4-aminobenzene dihydrochloride: 0.25 g
6-Methyl-1-hydroxy-3-aminobenzene: 0.02 g
2-Methyl-1,3-dihydroxybenzene: 0.15 g
1-Hydroxy-3-aminobenzene: 0.1 g
1,4-Dihydroxybenzene: 0.15 g
2-N-Methylamino-5-(β-hydroxyethoxy)-nitrobenzene: 0.3 g
2-N-Methylamino-5-methoxynitrobenzene: 0.25 g
2-N-(β-Hydroxyethyl)-amino-5-(N-methyl-N-β-hydroxyethyl)-aminonitrobenzene: 0.2 g
Oleyl alcohol glycerolated with 2 mols of glycerol: 5 g
Oleyl alcohol glycerolated with 4 mols of glycerol: 5 g
Oleic acid: 5 g
Oleyldiethanolamine: 5 g
Oleic diethanolamide: 12 g
Ethanol: 10 g
Ethylglycol: 12 g
Ethylenediaminetetraacetic acid: 0.2 g
35° Bé strength sodium bisulphite solution: 1.3 g
2-Amino-2-methylpropan-1-ol: 6 g
Distilled water, q.s.: 100 g This liquid is diluted with an equal weight of an oxidizing milk of 20 volumes strength in respect to hydrogen peroxide. After the gel obtained has been applied to blond hair for 30 minutes, the hair is rinsed, shampooed and dried. A coppery mahogany light blond shade is then obtained.

If the 2-amino-2-methylpropan-1-ol is replaced by ammonia, a change of the nitro dyestuffs into other nitro structures is observed during storage, and this change modifies the nature of the sheen obtained in the dyeing.

EXAMPLE 10

1,4-Diamino-2-methylbenzene: 0.4 g
1-Amino-4-hydroxybenzene: 0.1 g
1,3-Dihydroxybenzene: 0.45 g
1,4-Dihydroxybenzene: 0.1 g
2-N-Methylamino-5-(N-methyl-N-β,γ-dihydroxypropyl)-aminonitrobenzene hydrochloride monohydrate: 0.25 g
Oleyl alcohol glycerolated with 2 mols of glycerol: 5 g
Oleyl alcohol glycerolated with 4 mols of glycerol: 5 g
Oleic acid: 5 g
Oleyldiethanolamine: 5 g
Oleic diethanolamide: 12 g
Ethanol: 10 g
Ethylglycol: 12 g
Ethylenediaminetetraacetic acid: 0.2 g
35° Bé strength sodium bisulphite solution: 1.3 g
N-Methylethanolamine: 8 g Distilled water, q.s.: 100 g The above composition is diluted at the time of use with an equal weight of hydrogen peroxide of 20 volumes strength.

The gel obtained is applied to chestnut hair for 30 minutes. After rinsing, the hair is washed and then dried. It is then coloured an ashen light chestnut shade.

This composition makes it possible to obtain a storage stability of the nitro dyestuff which is much better than that which would be obtained using ammonia as the alkaline lightening agent.

Preparation of the 2-N-methylamino-5-(N-methyl-N-β,γ-dihydroxypropyl)-aminonitrobenzene hydrochloride monohydrate used in Example 10.

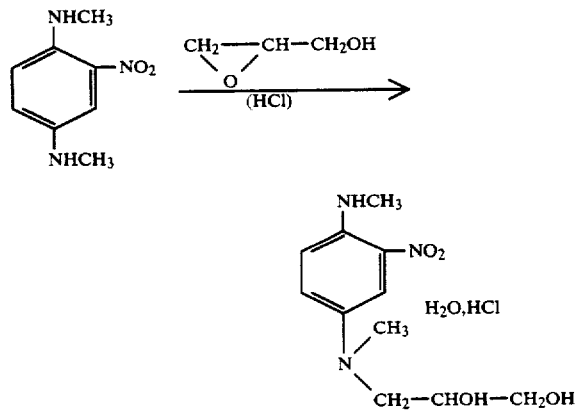

0.6 Mol (108.6 g) of 2-N-methylamino-5-N-methylaminonitrobenzene is introduced into 220 ml of ethanol. This mixture is first heated to the reflux temperature and 0.8 mol (60.4 g) of glycidol in 60 ml of ethanol is then added in the course of 15 minutes, with stirring. After heating under reflux for 3 hours, the alcohol is driven off in vacuo, 350 ml of water are added and extraction is carried out with ethyl acetate. The ethyl acetate is driven off in vacuo and the residual violet oil is then dissolved in 200 ml of absolute alcohol. 100 ml of ice-cold ethanol saturated with hydrogen chloride are added. After cooling to $-10°$ C., the expected product crystallises in the form of the hydrochloride monohydrate. It is filtered off, washed with a small amount of absolute alcohol and dried in vacuo. It melts with decomposition at 153°–155° C.

The product obtained corresponds to the following analysis results:

| Analysis | Calculated for | Found |
|---|---|---|
| | $C_{11}H_{17}N_3O_4 \cdot HCL \cdot H_2O$ | |
| C % | 42.58 | 42.51 |
| H % | 6.45 | 6.23 |
| N % | 13.54 | 13.73 |
| O % | 25.80 | 25.43 |
| Cl % | 11.45 | 11.62 |

We claim:

1. A composition suitable for the oxidation dyeing of human hair which comprises about 0.001 to 10% by weight of at least one oxidation dyestuff precursor selected from the group consisting of oxidation bases, couplers, and mixtures of oxidation bases and couplers and about 0.01 to 3% by weight of at least one nitro direct dyestuff selected from the group consisting of N-substituted ortho-nitroanilines of the formula (I):

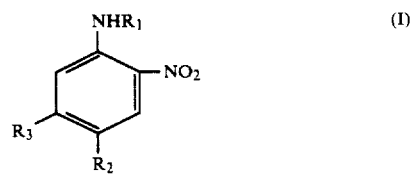

in which $R_1$ denotes a $(C_1-C_6)$ alkyl, monohydroxyalkyl or polyhydroxylalkyl group, $R_2$ denotes a hydrogen atom or an amino, mono-$(C_1-C_6)$alkylamino, di-$(C_1-C_6)$alkylamino, mono- or di-(monohydroxy$(C_1-C_6)$alkyl or polyhydroxy-$(C_1-C_6)$alkyl)-amino, N-$(C_1-C_6)$alkyl-N-monohydroxy-$(C_1-C_6)$-alkyl or N-$(C_1-C_6)$-alkyl-N-polyhydroxy-$(C_1-C_6)$-alkyl)-amino, $(C_1-C_6)$ alkoxy, monohydroxyalkoxy, polyhydroxyalkoxy or aminoalkoxy group and $R_3$ denotes a hydrogen atom or a $(C_1-C_6)$ alkyl group, at least one of $R_2$ and $R_3$ being different from hydrogen, with the proviso that if $R_1$ denotes the group —$CH_2CH_2OH$, $R_2$ does not denote a di-(monohydroxy-$C_1-C_6$)-alkyl)-amino group and cosmetically acceptable salts thereof, in an alkaline reducing medium which is non-ammoniacal and comprises about 0.1 to 4% by weight of an alkali metal or ammonium bisulphite and 0.1 to 30% by weight of at least one alkanolamine which is selected from the group consisting of N-($C_1$ to $C_4$-alkyl)-ethanolamines, N,N-di-($C_1$ to $C_4$-alkyl)-ethanolamines, di-(hydroxy-$C_2$ to $C_3$-alkyl)amines, 2-amino-2-methylpropan-1-ol, 2-dimethylamino-2-methyl-propan-1-ol, 2-amino-2-ethylpropane-1,3-diol, 2-amino-2-methylpropane-1,3-diol and 2-amino-2-hydroxymethylpropane-1,-3-diol.

2. A composition according to claim 1 in which the alkanolamine is selected from the group consisting of N-methylethanolamine, N-ethylethanolamine, N-propylethanolamine, N-isopropylethanolamine, N-butylethanolamine, N-tert.-butylethanolamine, N,N-dimethylethanolamine, N,N-diethylethanolamine, N-methyl-N-ethylethanolamine, N-methyl-N-propylethanolamine, diethanolamine, diisopropanolamine, 2-amino-2-methylpropan-1-ol, 2-dimethylamino-2-methylpropan-1-ol, 2-ethylpropan-1,3-diol, 2-amino-2-methylpropane-1,3-diol and 2-amino-2-hydroxymethyl propane-1,3-diol.

3. A composition according to claim 1 in which the bisulphite is sodium, potassium or ammonium bisulphite.

4. A composition according to claim 1, which comprises 0.05 to 2% by weight of dyestuff of formula (I), 0.01 to 5% by weight of oxidation dyestuff precursor, 1 to 25% by weight of alkanolamine and 0.2 to 2% by weight of alkali metal bisulphite, based on the total weight of the composition.

5. A composition according to claim 1 wherein said oxidation base is selected from the group consisting of para-phenylenediamine compounds, para-aminophenol compounds, para-diphenol compounds, ortho-aminophenol compounds, ortho-phenylenediamine compounds, pyridine bases and pyrimidine bases.

6. A composition according to claim 1 wherein said coupler is selected from the group consisting of phenol compounds, meta-diphenol compounds, meta-aminophenol compounds, meta-phenylenediamine compounds, monohydroxy or dihydroxy naphthalene compounds, heterocyclic couplers, pyrazolone compounds, and diketone compounds.

7. A composition according to claim 1 which further contains at least one surface-active agent, in an amount of 0.1 to 55% by weight, relative to the total weight of the composition.

8. A composition according to claim 7 which contains 1 to 40% by weight, relative to the total weight of the composition of the surface-active agent.

9. A composition according to claim 1 which further contains an organic solvent in an amount from 1 to 50% by weight, relative to the total weight of the composition.

10. A composition according to claim 9 which contains 3 to 30% by weight of said organic solvent, relative to the total weight of the composition.

11. A composition according to claim 1 which further contains a cationic polymer in an amount from 0.1 to 5% by weight, relative to the total weight of the composition.

12. A composition according to claim 1 which further contains a thickener in an amount from 0.1 to 5% by weight, relative to the total weight of the composition.

13. A composition according to claim 12 which contains said thickener in an amount from 0.5 to 3% by weight, relative to the total weight of the composition.

14. A composition according to claim 1 which has a pH of 8 to 11.5.

15. Process for dyeing human hair which comprises applying thereto a tinctorially effective amount of a composition as claimed in claim 1, mixed with an amount of an oxidising agent effective for developing coloration, leaving it on the hair for 2 minutes to 1 hour, rinsing the hair, optionally shampooing it and rinsing it again, and drying it.

16. Process according to claim 15 in which the mixed composition is left on the hair for 5 to 30 minutes.

* * * * *